United States Patent [19]

Ohshiro

[11] 4,168,702

[45] Sep. 25, 1979

[54] CAMERA OPERATING DEVICE FOR ENDOSCOPE

[75] Inventor: Susumu Ohshiro, Iwatsuki, Japan

[73] Assignee: Fuji Photo Optical Co., Ltd., Omiya, Japan

[21] Appl. No.: 801,337

[22] Filed: May 27, 1977

[30] Foreign Application Priority Data

May 27, 1976 [JP] Japan .................................. 51-60582

[51] Int. Cl.² ............................................. A61B 1/06
[52] U.S. Cl. ........................................ 128/6; 354/62
[58] Field of Search ..................... 128/4, 5, 6, 7, 8, 9, 128/10, 11, 16, 18, 303.1, 303.15; 354/62, 79, 266, 269; 350/19

[56] References Cited

U.S. PATENT DOCUMENTS

| 2,280,561 | 4/1942 | Wappler | 354/62 |
| 3,827,061 | 7/1974 | Kellner | 354/269 |

FOREIGN PATENT DOCUMENTS

| 1044348 | 11/1958 | Fed. Rep. of Germany | 128/4 |
| 426303 | 6/1967 | Switzerland | 354/79 |
| 496525 | 3/1976 | U.S.S.R. | 354/79 |

OTHER PUBLICATIONS

"Olympus ef Esophago Fiberscope", Medical-Surgical Review, First Quarter, 1969; (no page #).

Primary Examiner—Robert W. Michell
Assistant Examiner—Arthur S. Rose

[57] ABSTRACT

A photographic camera with a shutter release means is removably mounted on the eyepiece of an endoscope. Additional shutter release means is provided on the mounting body of the endoscope on which remote control means such as a dial for changing the direction of the head of the endoscope are mounted, whereby the shutter of the camera can be released without need for the operator to remove his hand from the vicinity of the remote control members.

4 Claims, 3 Drawing Figures

CAMERA OPERATING DEVICE FOR ENDOSCOPE

BACKGROUND OF THE INVENTION

1. Field of the Invention

This invention relates to an endoscope, and more particularly to an endoscope having an additional shutter release means for a photographic camera attached thereto.

2. Description of the Prior Art

In the medical field there are used endoscopes which are inserted into inaccessible places such as the human stomach and intestines for visual examination of these organs. Generally, the endoscope comprises a rigid head mounted on an end of a flexible tube which is inserted into the organs and through which the image of the organs is transmitted, and an eyepiece mounted on the opposite end thereof for viewing the image from the head. The head is mounted on one end of the flexible tube by way of a bendable portion which, in use, is bent to change the direction of the head. Adjacent to the eyepiece, a mounting body is provided between the eyepiece and an end of the flexible tube. On the mounting body is mounted remote control means such as an operating dial for controlling the direction of the head.

It is often desired to photograph the organ for subsequent inspection. When taking a picture of the organ, a photographic camera is connected to the eyepiece of the endoscope. Prior to taking the picture, the head must be inserted into the organ, then the part to be photographed is selected, for example, by bending the bendable portion, thereby changing the direction of the head, and, if desired, the part is cleaned by operating a cleaning mechanism. These operations are all performed by means of the remote control members viewing through the view finder of the camera, or the eyepiece of the endoscope as in case wherein the camera is attached after such operations. As mentioned above, the remote control members are disposed on the mounting body adjacent to the eyepiece of the endoscope.

Conventionally, when taking the picture, the shutter of the camera has been operated by means of the shutter release button which is inherent to the camera. It will be apparent that the shutter release button is remote from the remote control members of the endoscope. Therefore, there has been a problem in that the operator's hand must be replaced to depress the shutter release button from a position for operating the remote control members, accordingly, the head of the endoscope may be accidentally moved from the intended position.

SUMMARY OF THE INVENTION

Accordingly, the object of the present invention is to provide an endoscope having an additional shutter release means for the camera disposed adjacent to the remote control members on the mounting body, so that the shutter of the camera is made operable when the camera is mounted on the endoscope, without replacing the operator's hand from the position to operate the remote control members.

The endoscope in accordance with the present invention includes a shutter release means for actuating the shutter release circuit inherently provided in the camera body adapted to be attached to the endoscope, comprising a shutter release button depressable mounted on the mounting body thereof adjacent to the remote control members. The shutter release button is associated with an electrical switch means having a first pair of contacts which are put into contact with each other in response to a depression of the shutter release button. The first pair of contacts are respectively connected to a second pair of contacts by way of wire means and are adapted to be put into contact respectively with a third pair of contacts provided on the camera side when the camera is attached to the endoscope, said third pair of contacts being connected to the shutter control circuit provided in the camera so that the circuit is energized when they are operatively put into contact with each other.

Although above description is done in connection with an electric shutter, a mechanical shutter release means such as a shutter release cable should be used as an additional shutter release means in case of a mechanical shutter camera.

DESCRIPTION OF THE PREFERRED EMBODIMENT

Figure 1:
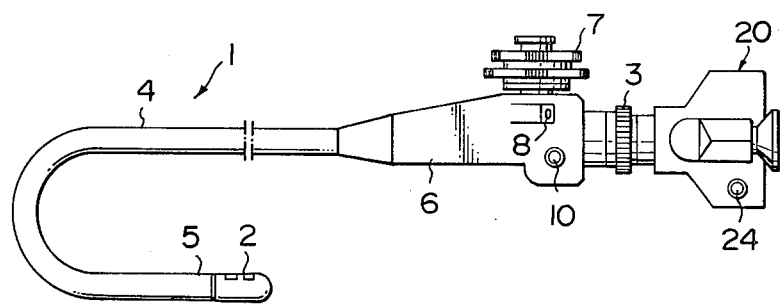
FIG. 1 is a plan view of an endoscope with a photographic camera attached in accordance with an embodiment of the present invention.

In FIG. 1, an endoscope in accordance with an embodiment of the present invention is shown with a photographic camera attached thereto.

An endoscope 1 of this embodiment includes as in a conventional one a head 2 through which an image of the object to be observed is transmitted to an eyepiece 3 which is disposed at an end of the endoscope opposite to the head 2. The head 2 is connected to the eyepiece 3 by way of an elongated flexible portion 4 and the image is transmitted from the head 2 to the eyepiece 3 through an optical fiber bundle (not shown) contained in the flexible portion 4. The head 2 is mounted on one end of the flexible portion 4 by way of a bendable portion 5 which, in use, is bent to change the direction of the head 2. Adjacent to the eyepiece 3 is provided a mounting body 6 on which are disposed remote control dials 7 which, for example, bend the bendable portion 5 to search the object to be observed and an inlet 8 for inserting a forceps therefrom. The mounting body 6 further includes, in accordance with the present invention, an additional shutter release button 10 slidable up and down which releases the shutter of the camera 20 when depressed as will be described in greater detail hereinbelow.

Figure 2:
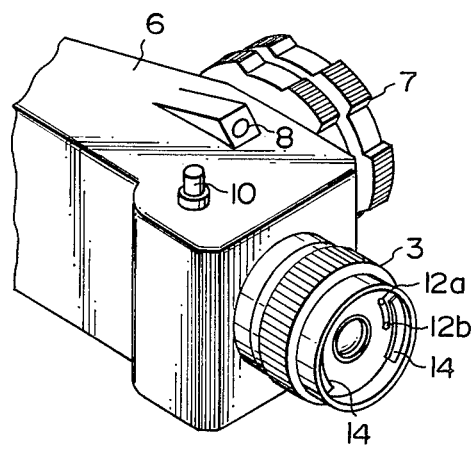
FIG. 2 is a fragmentary enlarged perspective view of FIG. 1.
Figure 3:
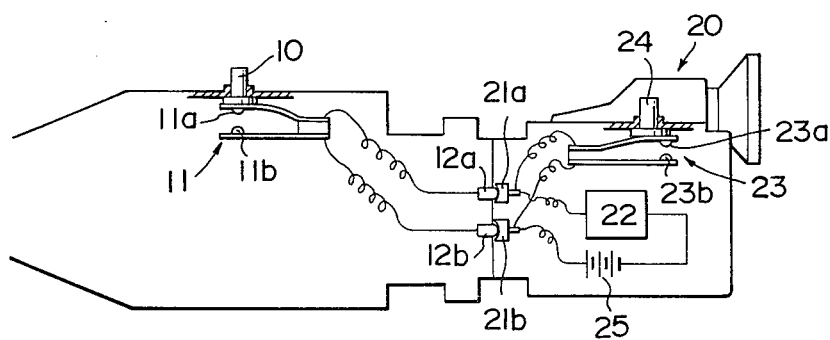
FIG. 3 is a somewhat diagrammatic side view for illustrating a shutter release means employed in the embodiment of FIG. 1.

As shown in FIG. 3, the shutter release button 10 is associated with an electrical switch 11 consisting of a first pair of contacts 11a and 11b so that when the shutter release button 10 is depressed the contacts 11a and 11b are put into contact with each other. The contacts 11a and 11b are respectively connected to a second pair of contacts 12a and 12b by way of wire means. The second pair of contacts 12a and 12b are secured to the front face of the eyepiece 3 as shown in FIG. 2.

On the other hand, a third pair of contacts 21a and 21b are provided on the front face of the camera 20. The contact 21a is directly connected to a shutter control circuit 22 of the camera 20 and the other contact 21b is connected to the shutter control circuit 22 by way of a power supply 23. The contacts 21a and 21b are respectively connected to a pair of contacts 23a and 23b of an electric switch 23 which are put into contact with each other when a shutter release button 24 inherent to the camera 20 is depressed.

Therefore, when the shutter release button 24 is depressed, the shutter control circuit is energized to close the shutter.

The camera 20 is adapted to be attached to the endoscope 1 by means of an engagement between a pair of bayonet craws 14 provided on the front face of the eyepiece 3 and corresponding bayonet craws (not shown) provided on the front face of the camera. When the camera 20 is attached to the endoscope 1, the second pair of contacts 12a and 12b are respectively put into contact with the third pair of contacts 21a and 21b, whereby the electrical switch 11 is connected to the shutter control circuit 22 in parallel to the electrical switch 23 in the camera body. Accordingly, either the additional shutter release button 10 or the shutter release button 24 inherent to the camera 20 may be depressed to release the shutter of the camera 20.

In case that the camera 20 includes a motor drive mechanism and if desired, the electrical switch 11 may be connected to the circuit (not shown) for controlling the motor drive mechanism so that the circuit is energized when the switch 11 is closed.

I claim:

1. An endoscope in combination with a photographic camera having a shutter release means in the camera, said endoscope comprising a head, a mounting body having an eyepiece, an optical fiber bundle connected between said head and said mounting body for transmitting an image of an object from the head to the eyepiece, remote control means such as a dial on said mounting body for controlling the direction of said head, and mounting means provided on the mounting body for demountably mounting said photographic camera on the eyepiece of the mounting body, wherein the improvement comprises camera operating means provided on the mounting body for operating the camera mounted on the eyepiece, connecting means provided in the mounting body, and said camera having connecting means operatively connected to said shutter release means in the camera and being positioned such that the connecting means automatically mates with the connecting means provided in said mounting body when the camera is mounted on the mounting body to automatically and operatively connect said camera operating means with the camera when the camera is mounted on the eyepiece, whereby the camera mounted on the eyepiece is operated by the camera operating means.

2. An endoscope in combination with photographic camera as defined in claim 1, in which said camera has a shutter, and said camera operating means is operative to release the shutter of said camera.

3. An endoscope in combination with a photographic camera as defined in claim 2, including a shutter release button which is depressably mounted on said mounting body adjacent to said remote control means, and said connecting means comprises an electrical switch means having a first pair of contacts and associated with the shutter release button so that the first pair of electrical contacts are put into contact with each other when the shutter release button is depressed, a second pair of electrical contacts disposed on the front face of said eyepiece, a third pair of electrical contacts disposed on the camera side, said shutter release means comprising a shutter control circuit in the camera, said second pair of electrical contacts being adapted to be put into contact respectively with said third pair of electrical contacts when the camera is mounted on the eyepiece, said second pair of contacts being operatively connected to the first pair of contacts and said third pair of contacts being connected to the shutter control circuit so that the circuit may be energized when the third pair of contacts are operatively put into contact with each other, whereby the shutter control circuit is energized when said shutter release button is depressed.

4. An endoscope in combination with a photographic camera as defined in claim 3 in which a normally opened electric switch is operatively connected to said third pair of contacts, and a shutter release button is provided on the camera for closing said electric switch in response to the depression of the shutter release button provided on the camera, whereby the shutter of the camera can be released either by the shutter release button provided on the mounting body of the endoscope or by the shutter release button provided on the camera.

* * * * *